United States Patent [19]

Jarvik

[11] Patent Number: 5,507,629
[45] Date of Patent: Apr. 16, 1996

[54] ARTIFICIAL HEARTS WITH PERMANENT MAGNET BEARINGS

[76] Inventor: Robert Jarvik, 124 W. 60 St., New York, N.Y. 10023

[21] Appl. No.: 261,858

[22] Filed: Jun. 17, 1994

[51] Int. Cl.$^6$ .................................................. F04B 35/04
[52] U.S. Cl. ...................... 417/423.3; 417/356; 417/365; 417/423.12; 415/900; 310/90.5; 384/907.1; 623/3
[58] Field of Search ....................... 417/356, 365, 417/423.3, 423.12; 415/900; 623/3; 310/90.5; 384/907.1

[56] References Cited

U.S. PATENT DOCUMENTS

| | | | |
|---|---|---|---|
| 4,057,369 | 11/1977 | Isenberg et al. | 417/365 |
| 4,688,998 | 8/1987 | Olsen et al. | 417/356 |
| 4,763,032 | 8/1988 | Bramm et al. | 310/90.5 |
| 4,779,614 | 10/1988 | Moise | 600/16 |
| 4,789,251 | 12/1988 | McPherson et al. | 384/907.1 |
| 4,994,078 | 2/1991 | Jarvik | 623/3 |
| 5,092,879 | 3/1992 | Jarvik | 623/3 |
| 5,182,533 | 1/1993 | Ritts | 310/90.5 |
| 5,342,825 | 8/1994 | Iannello et al. | 310/90.5 |

FOREIGN PATENT DOCUMENTS 963993  7/1964  United Kingdom .................. 417/365

*Primary Examiner*—Charles Freay

[57] ABSTRACT

Highly-miniaturized rotary artificial hearts small enough to be implanted within the natural heart are provided. The entire radial load of a high-speed pump rotor and most of the axial load is carried by a radially stable arrangement of high-energy-product permanent magnets. The rotor is fully suspended and rotated magnetically, with the exception of a single thrust-bearing contact point which utilizes ultra-hard, wear-resistant material, preferentially diamond, located at the axis of rotation in a high-flow region of the pump. No sensors or electromagnets are required for the bearings. One preferred embodiment utilizes dual mirror-image axial or mixed flow impellers mounted on a single axis so as to pump from a central inflow port out both ends of the device. This achieves thrust balancing, reduces pump speed by approximately half for a given flow and pressure, and is well-accommodated anatomically with double outflow grafts, one anastomosed directly to the aorta within the heart, and the second connected via the apex to the descending thoracic aorta.

11 Claims, 2 Drawing Sheets

U.S. Patent    Apr. 16, 1996    Sheet 1 of 2    5,507,629
FIG 1
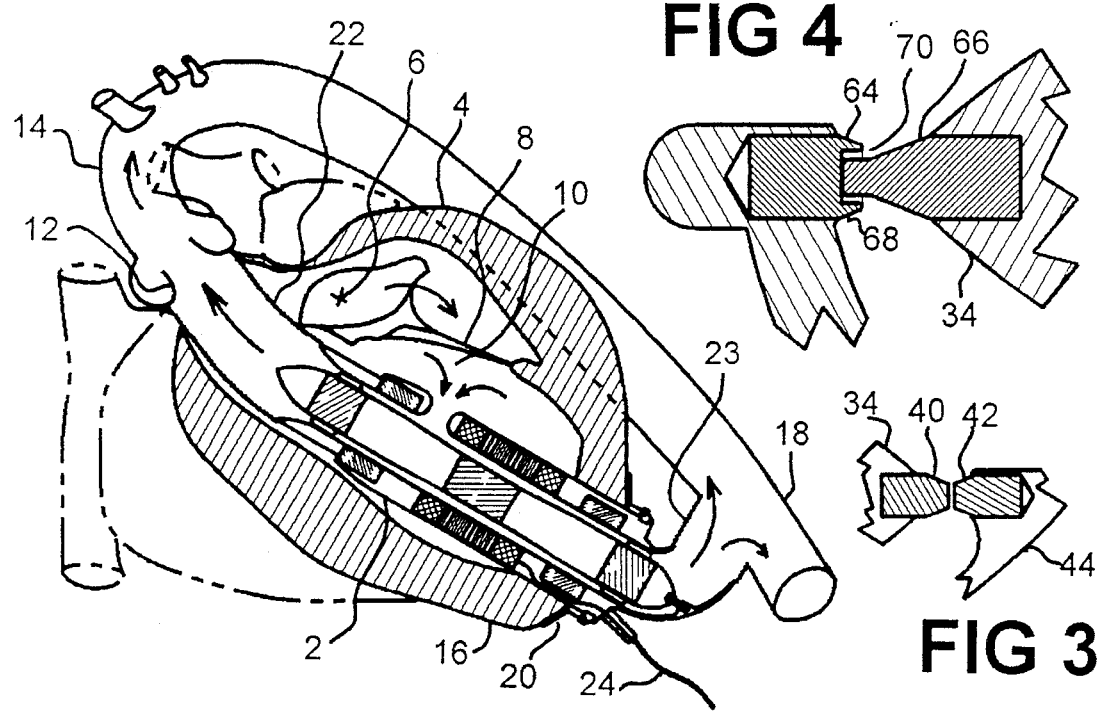
FIG 4
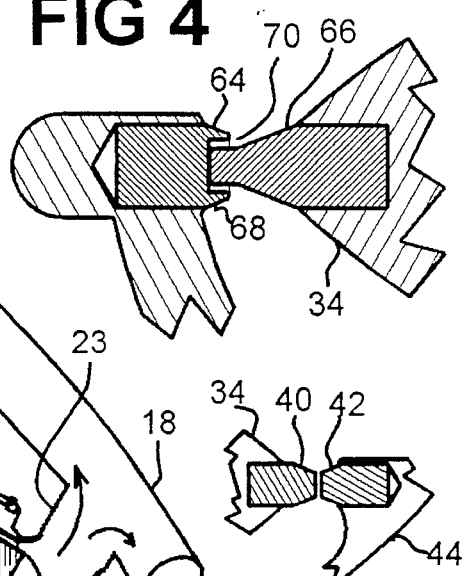
FIG 3
FIG 2
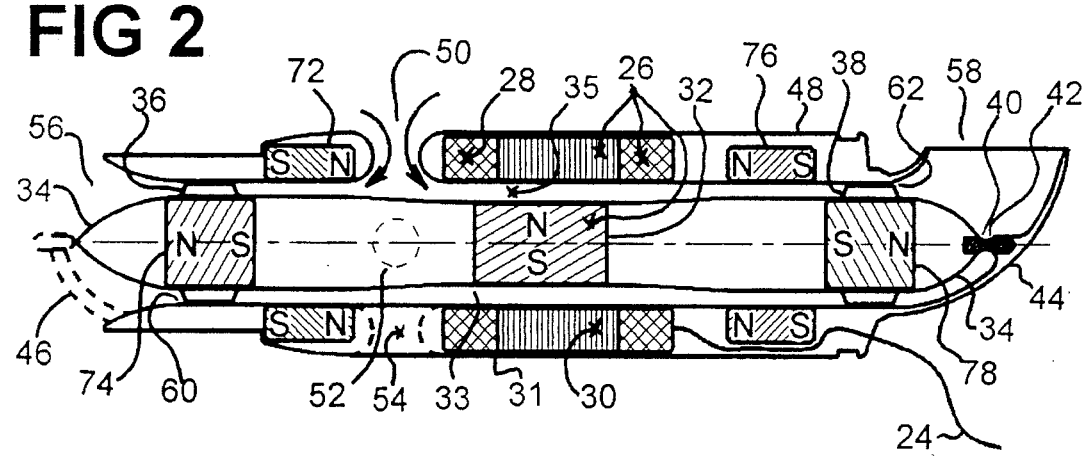

ARTIFICIAL HEARTS WITH PERMANENT MAGNET BEARINGS

BACKGROUND OF THE INVENTION

This invention relates to rotary artificial hearts which utilize centrifugal-flow, mixed-flow, or axial-flow pumps, principally driven by electric motors. Many such pumps are either in use for temporary blood pumping, such as with the heart lung machine, or under investigation for long-term use, such as those disclosed in prior U.S. Pat. Nos. 4,994,078 and 5,092,879 by the present inventor. Intraventricular axial-flow-pump, left-heart assist devices as disclosed in these patents have been successfully implanted in experimental animals for months with negligible blood damage, and have functioned in bench durability tests for years. The ultimate goal is to support human patients literally for decades, and although the use of properly designed mechanical radial bearings may accomplish this, magnetic suspension has the advantage of reduced wear with the greatest long-term durability potential.

Previous attempts to accomplish magnetic suspension in artificial hearts have required position sensors and electromagnets to stabilize at least one degree of freedom of the rotor. U.S. Pat. Nos. 4,688,998 by Olsen et al., 4,763,032 by Bramm et al., and 4,779,614 by Moise, each provide full, three-dimensional magnetic suspension of the rotor with electromagnetically-actuated rotor position adjustment with feedback control based on sensing motion of the rotor, either out of radial center or out of optimal axial position. The disadvantages of electromagnetically-actuated feedback control include the need for electromagnetic actuators, sensors and control circuitry, all of which add volume, weight, and complexity to the device and consume electric power. The present invention retains the rotor in optimal radial and axial position at all times. No sensors are used to measure rotor malposition because malposition never occurs. The rotor is suspended radially, and magnetically biased in one axial direction. Axial position is held by a single-point contact thrust bearing, and all thrust forces on the rotor, including those resulting from the hydrodynamic interaction of the impeller with the blood, are maintained below the force required to displace the thrust bearing from contact. Furthermore, when thrust balancing of the pump impellers is used, force on the thrust bearing is minimized. Since the thrust-bearing contact point is at the center of rotation, surface friction, wear, and heat generation are also minimized. Also, the thrust bearing point is located in a high-flow position for sufficient washing to prevent thrombus accumulation.

The magnetic bearing of the present invention may be used with centrifugal pumps and may also incorporate mechanical radial position limiters to maintain alignment of the rotor in nearly centered radial position if transient forces momentarily overcome the magnetic radial bearing capacity. Such mechanical limiters may take the form of mechanical radial bearings having a large enough radial clearance between the stationary and rotating members so that in usual operation they do not support the radial load and do not wear. In axial pump configurations, the impeller blades may be configured such that the rotor is mechanically supported by contact between the impeller tips and the housing within which the impeller rotates during transient conditions where radial load exceeds the magnetic bearing capacity. The blades may be composed of wear-resistant materials, such as ceramic, or may utilize wear-resistant inserts, and the housing bore in proximity to the blades may also be fabricated of wear-resistant materials. Thus, even with occasional mechanical contact, no galling of the surfaces or other damage to the pump will occur.

OBJECTS OF THE INVENTION

The major objects of the present invention include, but are not limited to, the following;

1) to provide a permanent magnetic bearing system requiring no electric power input, which fully suspends the radial load of a rotating object, provides partial magnetic thrust bearing capacity, and maintains axial position of the object by means of the simplest possible mechanical thrust bearing.

2) to provide a miniature and extremely durable blood pump for highly reliable long-term use.

3) to provide a blood pump utilizing nearly complete magnetic suspension of a rotating pump impeller combined with the most minimal mechanical thrust-bearing component possible.

4) to provide a dual-outlet artificial heart capable of operation at approximately half the rotational speed of a single-outlet device of comparable diameter.

5) to provide a radially magnetically suspended blood-pump rotor having near perfect thrust balancing to permit effective operation with minimal thrust-load variation under pulsatile flow conditions.

6) to provide a radially magnetically suspended blood-pump rotor having mechanical bearing safety backup capability during conditions of transient magnetic bearing overload.

7) to provide a magnetic bearing system capable of fully supporting a rotating load utilizing only permanent magnets without the need for position sensors and electromagnets to achieve bearing stability.

THE DRAWINGS

FIG. 1 is a schematic drawing of a natural heart with the left ventricle and implanted blood pump shown in longitudinal section.

FIG. 2 is a longitudinal section of a generally cylindrical blood pump illustrating the arrangement of the rotor and bearing components within the housing.

FIG. 3 is an enlarged sectional drawing of the mechanical thrust bearing used in the embodiment illustrated in FIG. 1.

FIG. 4 is an enlarged longitudinal section of a bearing having both thrust-bearing capacity and radial position-limiting capacity.

GENERAL DESCRIPTION OF THE INVENTION

Figure 5:
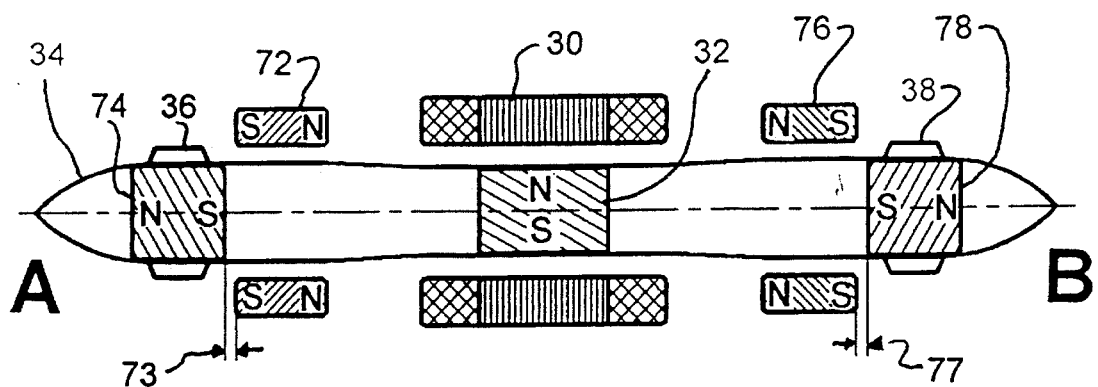
FIG. 5 is an illustration of a magnet and rotor configuration with no mechanical bearing contact.

An embodiment of the invention in which a blood pump with a magnetically-supported rotor carrying dual axial-flow pump impellers is implanted within the left ventricle of the heart is illustrated in FIG. 1. The device 2, which is generally cylindrical in shape, is contained within the cavity of the left ventricle 4, the wall of which is shown in section. Blood which enters the left ventricle enters through the mitral valve orifice 6, across the mitral valve leaflets and chordae tendineae 8 and into the device as shown by arrows 10. The path of the blood-stream is then divided, and approximately equal flow is ejected across the aortic valve 12 into the ascending aorta 14 and across the apex 16 into the descending thoracic aorta 18. In this configuration, the inflow consists only of side holes in the central portion of the pump housing, but in other configurations where the pump is placed outside the heart, an inflow tube is provided, such that the overall device configuration resembles the letter T. Still referring to FIG. 1, the device is affixed to the apex 16 by means of a sewing cuff 20. One outflow graft 22, typically of woven polyester is sutured to the aorta where it exits the ventricle, and another outflow graft 23 is sutured to the descending aorta. An electric cable 24, which provides power to the motor 26 exits the device near the apex.

Referring to FIG. 2, the electric motor 26 includes an armature having windings 28 and laminations 30, and one or more motor magnets affixed to the pump rotor and located generally within the bore of the armature. In this embodiment, a solid cylinder 32 of high-energy-product magnet material, such as neodyminium iron boron magnetized at right angles to the rotary axis of the motor, is used. Thus, the motor magnet has two poles, shown as N and S. To avoid corrosion and provide excellent blood compatibility of the pump, all magnets and motor components are encased in titanium which may be welded to provide a permanent seal. The space 35 between the motor armature and the motor rotor is generally referred to as the gap between the motor windings and motor magnet. In this embodiment, blood flows through the gap between the motor windings and motor magnet. In other embodiments, including devices utilizing centrifugal rather than axial flow pumps, magnetic couplings may be used to drive the pump rotor rather than have blood flow directly through the gap between the motor windings and motor magnet.

The pump rotor assembly 34 carries the motor magnet 32, bearing magnets 74, and 78, impellers 36 and 38, and may carry one or two wear-resistant bearing components 40, located at the pointed tip of the rotor at the center of its axis of rotation. In embodiments where mechanical thrust bearings are provided at each end of the rotor, the stationary bearing components may be mounted into the wall of a portion of the outflow passage of the pump generally formed as an elbow 44, or may be mounted on a streamlined strut 46 (illustrated in dotted lines to indicate that it is not part of the specific embodiment of FIG. 2) which projects into a generally cylindrical outflow passage within the vascular graft. Alternatively, two outflow elbows may be used, one at each end of the pump, and rather than suture one of the outflow grafts to the aorta inside the ventricle, this graft may pass through the wall of the ventricle and be sutured to the ascending aorta, thus preserving the ability of the natural heart to eject blood directly through the aortic valve without the blood first passing through the pump.

Figure 7:
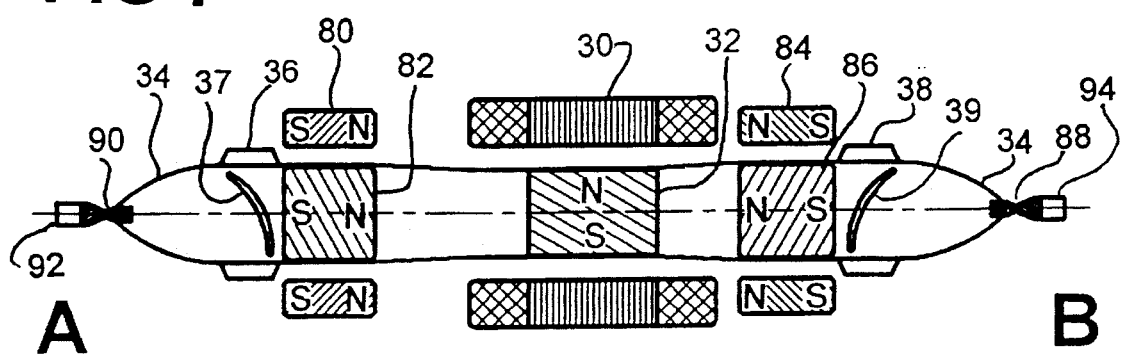
FIG. 7 is an illustration of the magnet and rotor configuration for an embodiment of the invention using two mechanical thrust bearings to confine the rotor.

The motor armature and stationary magnets 72, and 76 of the magnetic bearing system are affixed in position within the pump housing 48 which acts as a frame supporting them. One or more inflow openings 50, 52, 54 are located between the two impellers, and the two outflow openings 56 and 58 are near opposite ends of the rotor. The impellers, each of which may typically have several blades, are configured to pump away from the central inflow openings and toward both ends of the rotor, which rotates in only one direction. Thus, if blades are utilized on the impellers (some bladeless centrifugal devices can be used) they generally must be mirror-image shapes as best seen in FIG. 7 comparing blade contours 37 and 39.

The portions of the bore of the housing within which the impellers rotate are cylindrical and machined to a close tolerance. There is a gap between each impeller tip and the housing 60, 62 and the radial distance of the gap is the tip clearance. Generally, in magnetically-suspended axial flow pumps, this tip clearance is relatively large, such as 0.015" compared to only 0.003" in pumps that utilize mechanical radial bearings. This prevents contact of the blade tips with the housing where the magnetic fields are not perfectly symmetrical and the rotor runs slightly off center, as well as for other reasons, such as gradational force on the rotor. The rotor may incorporate foam or sealed air pockets to increase its buoyancy in blood and reduce the gradational force on the magnetic bearings, helping the rotor run more nearly centered.

Still referring to the embodiment shown in FIG. 2, the position of the rotor within the housing is maintained in the proper axial relationship by a magnetic force that axially presses the rotor against the thrust bearing at the contact of components 40 and 42. This axial force results from the position of the motor magnet relative to the motor laminations. The end of the magnet 33 protrudes beyond the end of the lamination stack 31 on one side but not on the other and therefore a net magnetic force acts axially pushing the rotor against the stationary thrust bearing. In the dual-outlet pump arrangement, the axial-thrust loads resulting from the actions of the impellers against the fluid are closely counterbalanced, and the magnetic axial-thrust load is sufficient to maintain the stable axial position of the rotor. Depending on the particular arrangement of magnets used to create the radial load bearing capability of the system, there may be additional magnetic axial force holding the rotor against the thrust bearings.

A very simple and effective thrust bearing design is illustrated in FIG. 3. Two small, wear-resistant inserts 40 and 42 are bonded into the rotor 34 and housing 44 and are preferably composed of diamond or ceramic. They contact one another on a small flat surface. This contact surface is a disc about 0.030" diameter. If the rotor is rotated at speeds of about 10–12,000 RPM the surface rubbing speed at the outer edge of the contact area is only about 2 ft/sec. and wear is negligible because the load is light, being no more than a few ounces. The very simple geometry of the inserts makes it practical to fabricate them out of single crystal diamond.

FIG. 4 illustrates a thrust bearing design which provides radial position limitation in addition to purely axial thrust bearing capability. Wear-resistant inserts 64 and 66 are mounted in the rotor 34 and bearing support strut 46 or housing. Thrust load is absorbed by a small disc-shaped contact surface, and under usual conditions of operation this is the only mechanical contact between the two inserts. Insert 64 has a shallow hole cut into it which creates a lip 68 radially surrounding a cylindrical portion of insert 66. The radial gap 70, between inserts 64 and 66, is much larger than the gap that would be used for a typical radial bearing. For example, in a pump having an impeller tip clearance of 0.015", the radial dimension of position limiter gap 70 may be 0.012". Thus, the rotor may rotate as much as 0.011" out of center with no radial contact at the bearings. With high-energy-product magnets in optimal configurations, this degree of magnetic centering can be achieved. However, if under transient load conditions the rotor moves 0.012" out of center, bearing insert 66 will contact the lip 68 of bearing insert 64 and mechanically limit further radial motion of the rotor. This will prevent the tips of the impellers from contacting the bore of the housing, as a tip clearance gap of 0.003" will be present at the closest point between the blade tips and the housing. Thus, the invention distinguishes the radial position limiter disclosed from a standard journal bearing with radial contact. For example, in pumps using mechanical radial bearings of the type disclosed in my U.S. Pat. No. 4,994,078, with a shaft 0.037" in diameter, the radial gap between the shaft and bearing sleeve surrounding it is only 0.0002". That is, the bearing gap is 60 times smaller than the gap used for the position limiter described.

Figure 6:
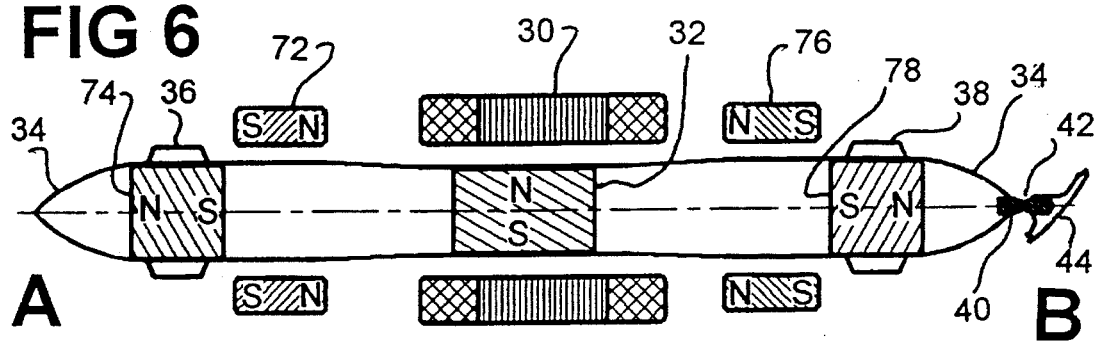
FIG. 6 is an illustration of the magnet and rotor configuration for an embodiment of the invention using one mechanical thrust bearing.

FIGS. 5, 6 and 7 illustrate arrangements of permanent magnets utilized to achieve magnetic bearing support of the rotors of several embodiments of the invention. In FIG. 5, rotor 34 is supported at each end by radial magnetic forces acting between ring magnet 72 and bar magnet 74 at one end, and between ring magnet 76 and bar magnet 78 at the other end. With the magnetic poles oriented as shown, the repelling magnetic forces tend to center magnet 74 with respect to magnet 72 if the axis of each is aligned. A thrust force of repulsion is also exerted between magnets 72 and 74 which, in the absence of any other forces on the rotor, would push the rotor towards the end labeled A in FIG. 5. The same situation exists with regard to magnets 76 and 78 at the other end of the device labeled B. The forces of repulsion exert a tension load on the portion of the rotor between magnets 74 and 78 and also apply a compression load to the housing to which stationary ring magnets 72 and 76 are affixed. There is only one position where the forces between these four magnets, the rotor itself, and the housing are balanced absent other forces related to the motor, the fluid, gravity, etc. This position is that shown in FIG. 5. As long as the rotor remains very close to this position axial forces tending to move the rotor in either direction are opposed by repulsive magnetic forces acting between magnets 72 and 74, and magnets 76 and 78. Because magnets 74 and 78 both protrude beyond the bore of magnets 72 and 76 there are gaps 73 and 77 present when the rotor is in the position shown in FIG. 5. Since magnets 74 and 78 are held at a fixed distance from one another by the rotor which acts as a rigid support frame, if magnet 74 is pushed axially closer to magnet 72 and thus gap 73 becomes smaller, magnet 78 must move away from magnet 76 and gap 77 must become larger. When this occurs, the magnetic force of repulsion between magnets 74 and 72 tending to move the rotor in the direction from B to A is increased while the force of repulsion acting between magnets 76 and 78 tending to move the rotor in the direction from A to B is decreased. Thus the rotor position shown in FIG. 5 is stable under low enough axial loads. Under high enough axial loads, if the entire rotor were permitted to move axially in either direction further away from the position shown in FIG. 5, it would reach a position where the axial forces would become unbalanced and tend to displace the rotor further axially from the balance position, until the south pole of the bar magnet on one end of the rotor moved to the position closest to the north pole of the ring magnet fixed in the housing. As this occurred, radial centering forces would be lost and the rotor would come to rest pressed against one side of the bore with the bar magnet at one end located fully within the ring magnet on that side.

With the motor present as shown in FIG. 5 and the motor magnet 32 centered axially within the motor laminations 30, there is no axial magnetic force exerted between the magnet and the laminations. However, if the rotor is moved axially in either direction, there is a magnetic force tending to move it back to the position where it is axially centered. This increases the stability of the overall configuration. Although the motor magnet seeks a stable axially-centered position, radially if it is out of center at all it will be attracted to the closest portion of the bore of the laminations. This creates a radial load which is supported by the forces between the ring magnets and the bar magnets at each end of the rotor.

With the system shown in FIG. 5, provided the magnetic strengths and radial symmetry of magnetization of all the components are properly adjusted, only magnetic forces from permanent magnets are required to provide completely balanced axial and radial forces to suspend the rotor. However, Bramm et al., in prior art U.S. Pat. No. 4,763,032 (column 3) state "a stable suspension of the rotor by means of permanent magnets is impossible by the Earnshaw Theorem alone, according to which each mechanical system which is held balanced in space (3 dimensions) only by means of permanent magnets is unstable". The arrangement illustrated in FIG. 5 represents an exception to the Earnshaw Theorem, although the axial range of motion within which the rotor retains its axial stability is quite limited and it becomes unstable once moved out of this range. To overcome this instability, my invention provides mechanical thrust bearings to axially maintain the rotor in a position where the radial magnetic forces are balanced and stable, and the axial magnetic forces on the mechanical thrust bearings are very low.

FIG. 6 illustrates a practical embodiment of the invention which uses a very similar arrangement of magnets compared to FIG. 5. However, the motor magnet is offset from the laminations which causes a magnetic thrust force pushing the rotor in the direction from A to B. The rotor is prevented from moving out of the position where axial forces on the rotor caused by the radial bearing magnet pairs 72, 74 and 76, 78 are counterbalanced and null, by the thrust bearing inserts 40 and 42 retained by the housing at 44.

FIG. 7 illustrates another practical arrangement utilizing permanent magnet radial bearings and mechanical thrust bearings to retain the rotor in a position where the axial forces of the radial bearing magnets are essentially null. In this embodiment, ring magnet 80 is magnetized north/south as illustrated, and bar magnet 82 is located within its bore, with its magnetic poles oriented as shown. Considering only magnets 80 and 82, a strong radial centering force exists due to repulsive forces. However, if bar magnet 82 is either tilted with regard to the alignment of the axis of its rotation to the axis of the bore magnet 80, or displaceed axially, strong magnetic fields force it out of its axially centered and untilted position. In the complete bearing support system, rotor magnet 82 is effectively prevented from tilting because the other end of the rotor experiences strong magnetic centering forces between magnets 84 and 86. Thrust bearing sets 88 and 90 are provided to mechanically prevent axial displacement of the rotor by confining it between housing supports 92 and 94. The rotor is thus held in a position where it is supported radially, is free to rotate, and the thrust load on the mechanical thrust bearings due to magnets 80, 82, 84 and 86 is negligible.

Still another practical embodiment (not illustrated) uses an offset motor magnet and a single thrust bearing like the embodiment of FIG. 6, combined with ring and bar magnets arranged like magnet pairs 80, 82 and 84, 86 of FIG. 7.

The information disclosed in the description of the present invention is intended to be representative of the principles that I have described. It will thus be seen that the objects of the invention set forth above and those made apparent from the preceding description are efficiently obtained and that certain changes may be made in the above articles and constructions without departing from the scope of the invention. It is intended that all matter contained in the above description or shown in the accompanying drawings shall be interpreted as illustrative but not in a limiting sense. It is also understood that the following claims are intended to cover all of the generic and specific features of the invention herein described and all statements of the scope of the invention which, as a matter of language, might be said to fall there between.

I claim:

1. A rotary pump comprising;
   a. housing means adapted to contain a rotor therewithin,
   b. pump impeller means carried by a rotor,
   c. permanent magnet radial bearing means including stationary permanent magnets supported in said housing and rotating permanent magnets mounted to said rotor configured to support the entire radial load of said rotor during usual operation,
   d. mechanical thrust bearing means including a wear-resistant bearing member affixed to said rotor at one end of the axis of rotation of the rotor and a stationary wear resistant mechanical bearing member affixed to said housing in direct proximity thereto so as to carry the thrust load on the rotor while maintaining the rotor in such a position that the stationary and rotating permanent magnets of the radial bearing means are in stable functional alignment and,
   e. power means to impart rotational force to said rotor and thereby actuate said pump.

2. The rotary pump of claim 1 adapted to pump blood in which the contact surface area of said mechanical thrust bearing is minimized and said housing and rotor are configured to wash the mechanical thrust bearing with a stream of blood of high enough velocity to prevent thrombus accumulation severe enough to impair the function of the pump.

3. The rotary pump of claim 1 in which magnetic means are provided to bias said rotor axially such that the rotating and stationary surfaces of said thrust bearing are retained in contact with one another.

4. The rotary pump of claim 1 in which two mechanical thrust bearings are provided, one at each end of the axis of rotation of the rotor, and the rotor is thereby axially confined.

5. The rotary pump of claim 1 adapted to pump blood, in which two mechanical thrust bearings are provided, one at each end of the axis of rotation of the rotor, the rotor is thereby axially confined, and said rotor and housing are configured to wash both mechanical thrust bearings with a stream of blood of high enough velocity to prevent thrombus accumulation severe enough to impair the function of the pump.

6. The rotary pump of claim 1 in which mechanical radial position limiting means are provided, said means comprising mechanical radial bearing means having so large a gap between rotating and stationary components thereof that radial displacement of the rotor must exceed the radial displacement under usual magnetically supported radial load conditions before mechanical contact of the limiting means can occur.

7. A dual outlet rotary blood pump comprising;
   a. a housing having a central inlet through which blood enters and two outlets through which blood is ejected,
   b. a rotor disposed for rotation within said housing upon which two pump impellers are mounted,
   c. bearing means supporting said rotor for rotation within said housing,
   d. said impellers configured such that rotation of the rotor in one direction pumps blood from the central opening to both outlets,
   e. power means to impart rotational force to said rotor and thereby actuate said pump, and,
   f. connector means to surgically affix said blood pump to the vascular system so as to provide relatively low pressure blood to the central inlet and to connect each outlet to blood vessels at arterial pressure such that the thrust load on each impeller acts to counterbalance the thrust load on the other impeller.

8. A bearing and rotor system adapted to carry and drive the impeller of a rotary pump comprising;
   a. a stationary frame having permanent magnets affixed thereto,
   b. a rotor having permanent magnets mounted thereupon in a configuration that provides radial magnetic bearing support forces in combination with the magnetic fields produced by said permanent magnets mounted on said stationary frame,
   c. thrust bearing means mounted on the stationary frame and on each end of the rotor configured to confine the rotor axially in a position where it is radially supported by said magnetic radial bearing forces, and is free to rotate about its axis,
   in which mechanical radial position limiting means are provided, said means comprising mechanical radial bearing means having so large a gap between rotating and stationary components thereof that radial displacement of the rotor must exceed the radial displacement under usual magnetically supported radial load conditions before mechanical contact of the limiting means can occur.

9. A rotary blood pump comprising;
   a. a blood pumping rotor contained in a pump housing,
   b. permanent magnetic bearing means adapted to support the radial load of the rotor without any electromagnetic radial bearing components,
   c. mechanical or a combination of mechanical and permanent magnet axial thrust bearing means adapted to function without any electromagnetic thrust bearing components,
   d. power means to rotate the rotor and thereby pump the blood.

10. The blood pump of claim 9 in which the rotor includes a hydrodynamic impeller.

11. The rotary blood pump of claim 9 in which the power means includes an electric motor and some of the blood pumped passes through a channel within said electric motor.

* * * * *